US010646278B2

(12) United States Patent
Ikits et al.

(10) Patent No.: US 10,646,278 B2
(45) Date of Patent: *May 12, 2020

(54) SYSTEMS AND METHODS FOR PROSTHETIC COMPONENT ORIENTATION

(71) Applicant: MAKO Surgical Corp., Ft. Lauderdale, FL (US)

(72) Inventors: Milan Ikits, Plantation, FL (US); Jason Karl Otto, Plantation, FL (US); Carinne Cecile Granchi, Weston, FL (US); Ali Zafar Abbasi, Davie, FL (US)

(73) Assignee: MAKO Surgical Corp., Fort Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/434,229

(22) Filed: Jun. 7, 2019

(65) Prior Publication Data

US 2019/0282303 A1    Sep. 19, 2019

Related U.S. Application Data

(63) Continuation of application No. 13/339,524, filed on Dec. 29, 2011, now Pat. No. 10,314,653.

(51) Int. Cl.
*A61B 34/10* (2016.01)
*A61B 34/20* (2016.01)
*A61F 2/38* (2006.01)

(52) U.S. Cl.
CPC .............. *A61B 34/10* (2016.02); *A61B 34/20* (2016.02); *A61B 2034/101* (2016.02);
(Continued)

(58) Field of Classification Search
CPC .............. A61B 19/50; A61B 2019/501; A61B 2019/505; A61B 2019/504;
(Continued)

(56) References Cited

U.S. PATENT DOCUMENTS

| 5,880,976 A | 3/1999 | Digioia, III et al. |
| 6,554,837 B1 | 4/2003 | Hauri et al. |

(Continued)

FOREIGN PATENT DOCUMENTS

| CN | 101011299 A | 8/2007 |
| CN | 101959474 A | 1/2011 |

OTHER PUBLICATIONS

Communication on EP Application No. 12816398, dated Jan. 4, 2016, 4 pages.

(Continued)

*Primary Examiner* — Mohamed Charioui
*Assistant Examiner* — Jeremy A DeLozier
(74) *Attorney, Agent, or Firm* — Foley & Lardner LLP

(57) ABSTRACT

A computer-implemented method determines an orientation parameter value of a prosthetic component. The method includes receiving a first desired separation distance between a first prosthetic component and a second prosthetic component at a first flexion position of a flexion joint and estimating a first estimated separation distance between the first prosthetic component and the second prosthetic component at the first flexion position of the joint for at least one potential orientation of the first prosthetic component. The method also includes determining a first orientation parameter value of the first prosthetic component by comparing the first estimated separation distance to the first desired separation distance and outputting the first orientation parameter value via a user interface.

20 Claims, 7 Drawing Sheets

(52) U.S. Cl.
CPC ... *A61B 2034/102* (2016.02); *A61B 2034/104* (2016.02); *A61B 2034/105* (2016.02); *A61B 2034/108* (2016.02); *A61F 2002/3895* (2013.01)

(58) Field of Classification Search
CPC .......... A61B 2019/508; A61B 19/5244; A61B 2019/502; A61B 2002/3895; A61F 2002/3895
See application file for complete search history.

(56) References Cited

U.S. PATENT DOCUMENTS

| | | |
|---|---|---|
| 2005/0038442 A1 | 2/2005 | Freeman |
| 2006/0142657 A1 | 6/2006 | Quaid et al. |
| 2008/0262812 A1* | 10/2008 | Arata ................... G06F 19/00 703/11 |
| 2008/0269596 A1 | 10/2008 | Revie et al. |
| 2008/0319448 A1* | 12/2008 | Lavallee ................ G06F 17/50 606/102 |
| 2009/0318931 A1* | 12/2009 | Stone .................. A61B 17/175 606/102 |
| 2010/0010506 A1 | 1/2010 | Murphy |
| 2010/0137869 A1 | 6/2010 | Borja et al. |
| 2010/0153076 A1 | 6/2010 | Bellettre et al. |

OTHER PUBLICATIONS

Extended European Search Report for EP App. No. 17194440.8, dated May 30, 2018, 8 pages.
International Search Report and Written Opinion on PCT/US2012/070516, dated Mar. 22, 2013, 10 pages.

* cited by examiner

SYSTEMS AND METHODS FOR PROSTHETIC COMPONENT ORIENTATION

CROSS-REFERENCE TO RELATED APPLICATIONS

This application is a continuation of U.S. application Ser. No. 13/339,524, filed on Dec. 29, 2011, which is hereby incorporated by reference herein in its entirety.

BACKGROUND

The present disclosure relates generally to prosthetic component orientation systems and, more particularly, to systems for determining an orientation of one or more prosthetic implants to be used in knee joint replacement surgeries.

The knee joint includes the interface between the distal end of the femur and the proximal end of the tibia. In a properly-functioning knee joint, medial and lateral condyles of the femur pivot smoothly along menisci attached to respective medial and lateral condyles of the tibia. In certain knees, such as diseased arthritic knees, cartilage may have eroded, causing the space between the femur and the tibia to collapse and leading to bone-on-bone contact. When this happens, the natural bones and cartilage that form the joint may be unable to properly articulate, which can lead to joint pain and/or interfere with normal use of the joint.

In some situations, surgery is required to correct the alignment between the tibia and femur and restore normal use of the joint. Depending upon the severity of the damage, the surgery may involve partially or completely replacing the joint with prosthetic components. During such knee replacement procedures, a surgeon resects damaged portions of the bone and cartilage, while attempting to leave healthy tissue intact. The surgeon then fits the healthy tissue with artificial prosthetic components designed to replicate the resected tissue and restore proper knee joint operation.

The orientation of these prosthetic components on the tibia and/or femur may impact the alignment between the tibia and the femur and thus affect how the joint articulates. Improperly oriented prosthetic components may fail to restore proper knee joint operation and/or may cause premature component failure or deterioration, among other problems. Accordingly, proper orientation of these components is critical, and a surgeon may spend a great deal of time and effort determining the proper orientations of the prosthetic components before fitting them to the joint. However, even with the surgeon's experience, making such a determination manually may not result in an optimal, or even acceptable, location and orientation of the prosthetic components.

SUMMARY

According to one aspect, the present disclosure is directed to a computer-implemented method for determining an orientation parameter value of a prosthetic component. The method may include receiving a first desired separation distance between a tibial prosthetic component and a femoral prosthetic component at a first flexion position of a knee joint, and estimating a first estimated separation distance between the tibial prosthetic component and the femoral prosthetic component at the first flexion position of the knee joint for at least one potential orientation of the femoral prosthetic component. The method may also include determining a first orientation parameter value of the femoral prosthetic component by comparing the first estimated separation distance to the first desired separation distance, and outputting the first orientation parameter value via a user interface.

According to another aspect, the present disclosure is directed to a system for determining an orientation parameter value of a prosthetic component. The system may include an input device configured to receive a first desired separation distance between a tibial prosthetic component and a femoral prosthetic component at a first flexion position of a knee joint. The system may also include a processor that is operatively coupled to the input device. The processor may be configured to estimate a first estimated separation distance between the tibial prosthetic component and the femoral prosthetic component at the first flexion position of the knee joint for at least one potential orientation of the femoral prosthetic component, and determine a first orientation parameter value of the femoral prosthetic component by comparing the first estimated separation distance to the first desired separation distance. The system may also include a display operatively coupled to the processor and configured to output the first orientation parameter value.

According to another aspect, the present disclosure is directed to another computer-implemented method for determining an orientation of a prosthetic component. The method may include recording relative positions of a tibia and a femur at a plurality of flexion positions of the knee, and receiving a plurality of looseness values via a user interface, each of the plurality of looseness values corresponding to a looseness preference between the tibia and the femur for one of the plurality of flexion positions of the knee. The method may also include determining an orientation of a prosthetic component for the knee based on the recorded relative positions of the tibia and the femur and the received looseness values, and outputting the orientation of the prosthetic component via a display.

Additional objects and advantages of disclosed embodiments will be set forth in part in the description which follows, and in part will be obvious from the description, or may be learned by practice of the disclosed embodiments. The objects and advantages of the disclosed embodiments will be realized and attained by means of the elements and combinations particularly pointed out in the appended claims. It is to be understood that both the foregoing general description and the following detailed description are exemplary and explanatory only and are not restrictive of the disclosed embodiments, as claimed.

BRIEF DESCRIPTION OF THE FIGURES

The accompanying drawings, which are incorporated in and constitute a part of this specification, illustrate several embodiments that, together with the description, serve to explain the principles and features of the present disclosure.

DETAILED DESCRIPTION

Reference will now be made in detail to exemplary embodiments of the present disclosure, examples of which are illustrated in the accompanying drawings.

Figure 1:
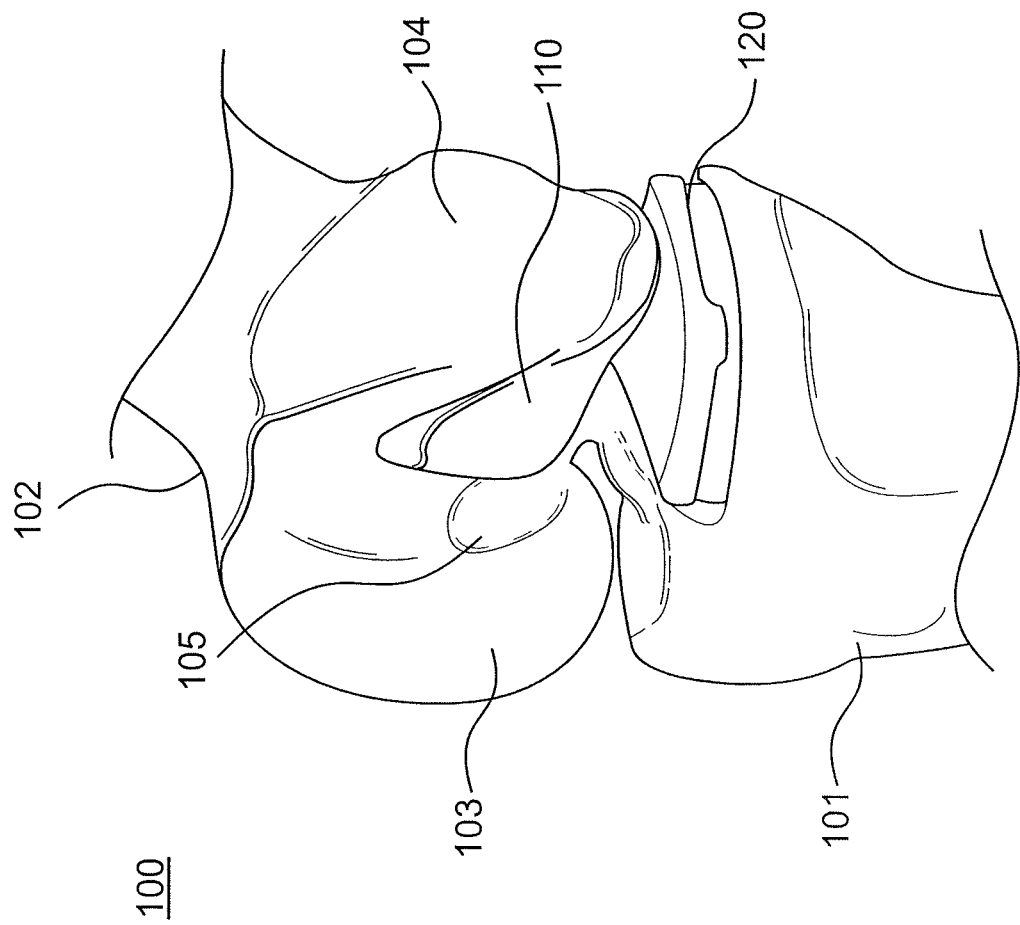
FIG. 1 illustrates a perspective view of post-operative prosthetic knee joint fitted with prosthetic components, consistent with disclosed embodiments.

FIG. 1 illustrates a perspective view of a post-operative prosthetic knee joint 100 fitted with prosthetic components 110 and 120, consistent with disclosed embodiments. Knee joint 100 includes a tibia 101 and a femur 102. Femur 102 may include a lateral condyle 103 and a medial condyle 104 separated by an intercondylar notch 105. Tibia 101 may likewise include a lateral condyle 106 and a medial condyle 107. During knee surgery, such as unicompartmental arthroplasty, prosthetic components may be fitted to one or more of lateral condyle 103, medial condyle 104, lateral condyle 106, and medial condyle 107. For example, FIG. 1 illustrates a femoral prosthetic component 110 fitted to medial condyle 104 of femur 102 and a tibial prosthetic component 120 fitted to medial condyle 107 of tibia 101.

Similar prosthetic components may also be fitted to lateral condyle 103 and/or lateral condyle 106. Further, the exemplary embodiments below refer to prosthetic components on the medial condyles merely for convenience, and those skilled in the art will appreciate that the disclosed embodiments apply to prosthetic components on the lateral condyles as well.

The orientation of femoral prosthetic component 110 and/or tibial prosthetic component 120 may impact the alignment between the tibia 101 and the femur 102 and affect how the knee joint 100 articulates. Thus, a surgeon generally determines the proper orientation of femoral prosthetic component 110 and/or tibial prosthetic component 120. Disclosed embodiments provide systems and methods to output orientations of one or more prosthetic components to the surgeon, such as the orientations of femoral prosthetic component 110 or tibial prosthetic component 120. In certain embodiments, the disclosed systems and methods may receive input from the surgeon, such as desired looseness or tightness values for the knee joint 100, and may determine the orientations based on this input from the surgeon. The system may use one or more optimization and/or minimization algorithms, discussed in greater detail below, to determine the orientations.

Figure 2:
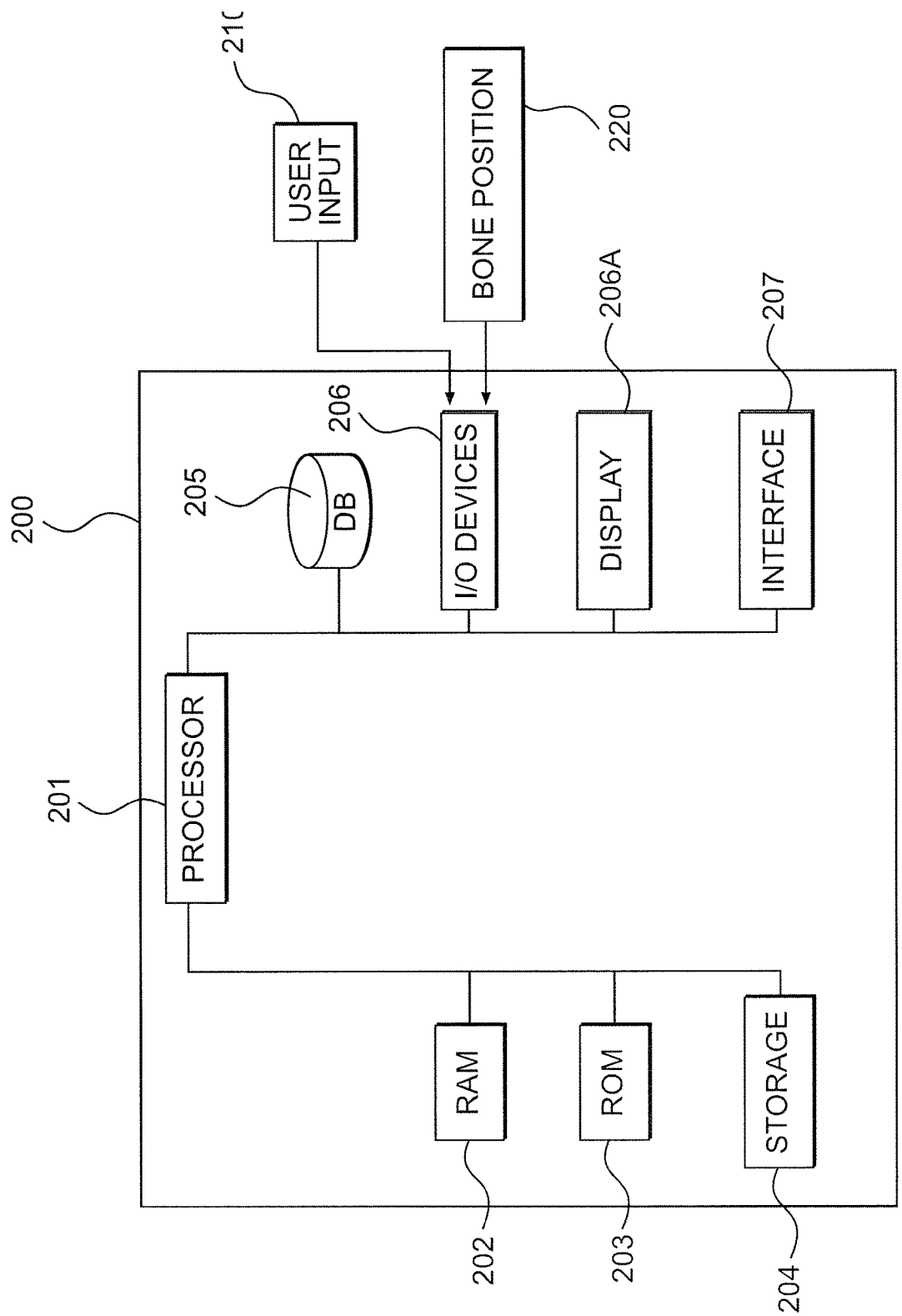
FIG. 2 is a schematic diagram of a computer system programmed to determine prosthetic component orientation, consistent with disclosed embodiments

FIG. 2 is a schematic diagram of an exemplary computer system 200 that may be used to determine prosthetic component orientation, consistent with disclosed embodiments. Computer system 200 may generally be operable to receive user input 210 corresponding to a desired looseness of the knee joint and bone position data 220 corresponding to relative positions of tibia 101 and femur 102. Computer system 200 may also be operable to output prosthetic component orientations via a display 206A or other input/output (I/O) devices 206 based on user input 210 and/or bone position data 220. In some embodiments, computer system 200 may be included in a computer-assisted surgery system, such as the RIO® Robotic Arm Interactive Orthopedic System by MAKO Surgical Corp. of Fort Lauderdale, Fla., as described, for example, in U.S. patent application Ser. No. 11/357,197 (U.S. Patent Application Pub. No. 2006/0142657), filed Feb. 21, 2006, which is hereby incorporated by reference herein in its entirety.

As shown in FIG. 2, computer system 200 may include a processor 201, a random access memory (RAM) module 202, a read-only memory (ROM) module 203, a storage device 204, a database 205, I/O devices 206, display 206A, and a network interface 207. Processor 201 may include one or more microprocessors configured to execute instructions and process data to perform one or more functions associated with computer system 200. Storage device 204 may include a volatile or non-volatile, magnetic, semiconductor, tape, optical, removable, nonremovable, or other type of storage device or computer-readable medium. RAM module 202 may include one or more programs or subprograms loaded from ROM module 203, storage device 204, or elsewhere that, when executed by processor 201, perform various procedures, operations, or processes consistent with disclosed embodiments. For example, RAM module 202 may include one or more programs that enable processor 201 to record relative positions of a tibia 101 and a femur 102 at a plurality of flexion positions of the knee joint 100 based on position data 220, receive looseness values as user input 210, determine an orientation of a prosthetic component for the knee joint 100 based on the recorded relative positions and the looseness values, and output the orientation information via display 206A.

I/O devices 206 may include any devices capable of receiving input from a user and sending output to the user. For example, I/O devices 206 may include a console with an integrated keyboard and mouse to allow a user, e.g., a surgeon, to input parameters such as desired looseness values or any other parameters. I/O devices 206 may also include display 206A that may display a graphical user interface (GUI) for outputting and receiving information. I/O devices 206 may also include peripheral devices such as, for example, a printer, a user-accessible disk drive (e.g., a USB port, a floppy, CD-ROM, or DVD-ROM drive, etc.), a microphone, a speaker system, or any other suitable type of interface device. For example, I/O devices 206 may include an electronic interface that allows a user to input patient data, such as computed tomography (CT) data into computer system 200 in order to generate three-dimensional models of the patient's anatomy in software, as discussed below.

Database 205 may be included in RAM module 202, ROM module 203, storage device 204, or elsewhere. In certain embodiments, database 205 may be located separately from computer system 200 and may be accessed via a network, e.g., by network interface 207. Database 205 may store one or more three-dimensional models representing various parts of a patient's anatomy, such as models of all or part of a patient's tibia, femur, knee joint, etc. These models may be developed, e.g., from data acquired using any combination of computed topography (CT), magnetic resonance imaging (MRI), positron emission tomography (PET), coordinated fluoroscopy, and angiographic data acquired before and/or during surgery. The three-dimensional models stored in database 205 may also include one or more points about the surface of the models. The points may be selected by a user or may be generated automatically by computer system 200 or another computer system, and may identify anatomical landmarks on the three-dimensional models, e.g., the center of a tibial condyle, a trochlear groove point on the femur, or any other landmark point.

In certain embodiments, the models may be direct representations of a patient's anatomy. For example, in one embodiment, the three-dimensional model may be constructed from a series of pre-operative CT scans taken at cross-sections along a patient's femur 102, knee joint 100, and tibia 101. In other embodiments, data points regarding features of the patient's anatomy may be determined using one or more of the above-described technologies, or any other technology, and the data points may be matched to one or more existing three-dimensional models in a library of three-dimensional models that may be stored at database 205 or elsewhere.

Database 205 may also store one or more three-dimensional models corresponding to one or more prosthetic components. For example, database 205 may include three-dimensional models of different tibial prosthetic components 120 and/or femoral prosthetic components 110. Separate models may be stored based on the manufacturer, model, and size of each implant. The models may be generated based on the technical specifications of each prosthetic component using computer-aided design (CAD) techniques, or any other technique. Computer system 200 may use the three-dimensional models of the patient's anatomy and the prosthetic components stored in database 205 when determining an orientation of one or more prosthetic components.

Exemplary features of system 200 will be discussed below with regard to FIGS. 2-5. The disclosure below discusses using system 200 to determine an orientation of the femoral prosthetic component 110 merely for convenience. Those skilled in the art will appreciate that the methods and systems described herein may also be used to determine the orientation of tibial prosthetic components 120 and are not limited to determining the orientation of femoral prosthetic components 110.

Prior to surgery, computer system 200 may use the three-dimensional models of the patient's anatomy and of the prosthetic components stored in database 205 to determine a preliminary orientation of one or more prosthetic components. For example, prior to surgery, computer system 200 may analyze the size, shape, and points identifying anatomical landmarks of the three-dimensional models to determine a preliminary orientation of femoral prosthetic component 110 and/or tibial prosthetic component 120. In certain embodiments, a surgeon may determine the preliminary orientation of femoral prosthetic component 110, and may send the preliminary orientation information to computer system 200, e.g., via one of I/O devices 206. In other embodiments, computer system 200 may determine the preliminary orientation of femoral prosthetic component 110 without input from a user.

During surgery, the user may interact with computer system 200 to record relative positions of femur 102 and tibia 101 at different flexion positions of knee joint 100. For example, a surgeon may apply a valgus/varus moment (i.e., a lateral force and a bending force) to knee joint 100 while moving the joint through a range of flexion positions. The valgus/varus moment may attempt to align femur 102 and tibia 101 to their correct relative positions as they would be in an undiseased, non-arthritic knee. Computer system 200 may record the relative positions of femur 102 and tibia 101 at the different flexion positions using, e.g., coordinated fluoroscopic imagery, or any other method. The data related to these relative positions may be stored in database 205 or elsewhere within computer system 200.

In some embodiments, the relative positions of femur 102 and tibia 101 may be recorded prior to the surgeon resecting the bones and installing the prosthetic devices. In other embodiments, however, the relative positions may be recorded after resecting one of the bones and implanting a prosthetic component. In these embodiments the computer system 200 may record the relative positions of the non-resected bone and the implanted prosthetic component. For example, if computer system 200 is being used to determine an orientation of a femoral prosthetic component, the surgeon may resect the damaged area on the tibia and implant the tibial prosthetic component prior to measuring the relative positions of the femur and the tibial prosthetic component.

Figure 3:
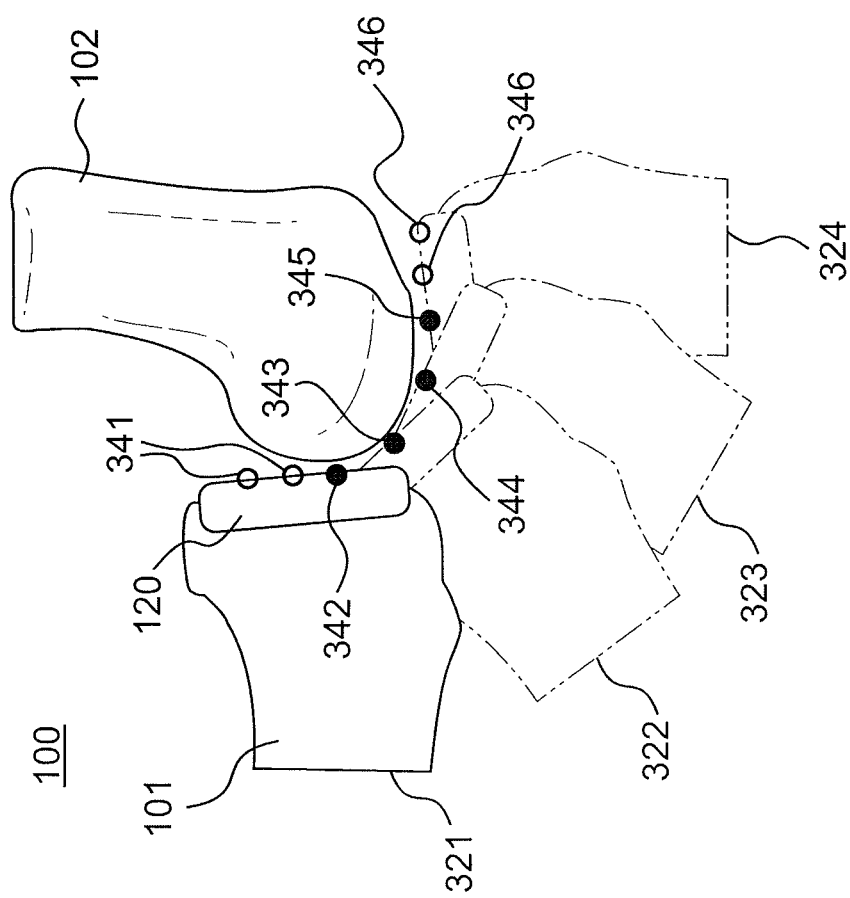
FIG. 3 illustrates side view of a knee joint at multiple different flexion positions, consistent with disclosed embodiments.

FIG. 3 illustrates a side view of knee joint 100 at multiple different flexion positions, as may be controlled by a surgeon when recording the relative positions of the femur 102 and the tibia 101, consistent with disclosed embodiments. As discussed above, the surgeon may manipulate the patient's leg to place tibia 101 in multiple different flexion positions such as positions 321, 322, 323, and 324 relative to femur 102. For example, position 321 illustrates approximately 90° flexion, position 322 illustrates approximately 60° flexion, position 323 illustrates approximately 30° flexion, and position 324 illustrates approximately 0° flexion or full extension, although any other positions and number of positions throughout the patient's range of motion may be used.

Computer system 200 may record relative positions of femur 102 and tibia 101 (or tibial prosthetic component 120) in each position 321-324. In FIG. 3, tibial prosthetic component 120 has already been installed. Accordingly, in the embodiment of FIG. 3, computer system 200 may record the relative positions of femur 102 and tibial prosthetic component 120. However, as discussed above, the relative positions of femur 102 and tibia 101 may be measured prior to resection and implanting tibial prosthetic component 120 and/or femoral prosthetic component 110.

Computer system 200 may record the relative positions of femur 102 and tibia 101 by measuring a distance between a predetermined point, e.g., one of points 342-345, on tibial prosthetic component 120 and a corresponding point on femur 102 for each flexion position. In one embodiment, the corresponding point on femur 102 may be a point on the surface of femur 102 that is closest to the one of points 342-345 being measured at that particular flexion position. Moreover, other methods may be used to determine the relative positions of femur 102 and tibia 101 (or tibial prosthetic component 120) in each position 321-324, such as using distances between multiple points, the distance between the point on femur 102 and the point on tibia 101 that are closest to each other, an average distance between curves representing femur 102 and tibia 101, etc.

The location of points 342-345 may be determined, e.g., based on the three-dimensional models of tibial prosthetic component 120 and/or tibia 101. For example, points 342-345 may correspond to anatomical landmarks of tibia 101 that may be stored in database 205, as discussed above. Similarly, points 342-345 may correspond to points on tibial prosthetic component 120 or tibia 101 that are located closest to femur 102.

In one embodiment, additional points may be used at certain flexion positions, such as a flexion position near 90° and a flexion position near 0°. For example, computer system 200 may record additional relative position data at points 341 for a near −90° flexion position and at points 346 for a near −0° flexion position. As shown in FIG. 3, points 341 may be located toward a posterior end of tibial prosthetic component 120, while points 346 may be located toward an anterior end of tibial prosthetic component 120. Recording relative position data at these points may allow computer system 200 to ensure, e.g., that an orientation of the femoral prosthetic component does not interfere with tibial prosthetic component 120 at certain flexion positions. Those skilled in the art will appreciate that the various flexion positions mentioned herein are approximations that are made, e.g., by the surgeon when applying the valgus/varus moment to the knee joint. As such, the actual flexion positions of the knee joint 100 may vary on the order of several degrees.

Once the relative positioning data is collected, this data may be stored at database 205 or elsewhere. The relative positioning data may be used by computer system 200 in combination with user input to determine orientations for one or more prosthetic components, such as femoral prosthetic component 110, discussed in greater detail below.

Figure 4:
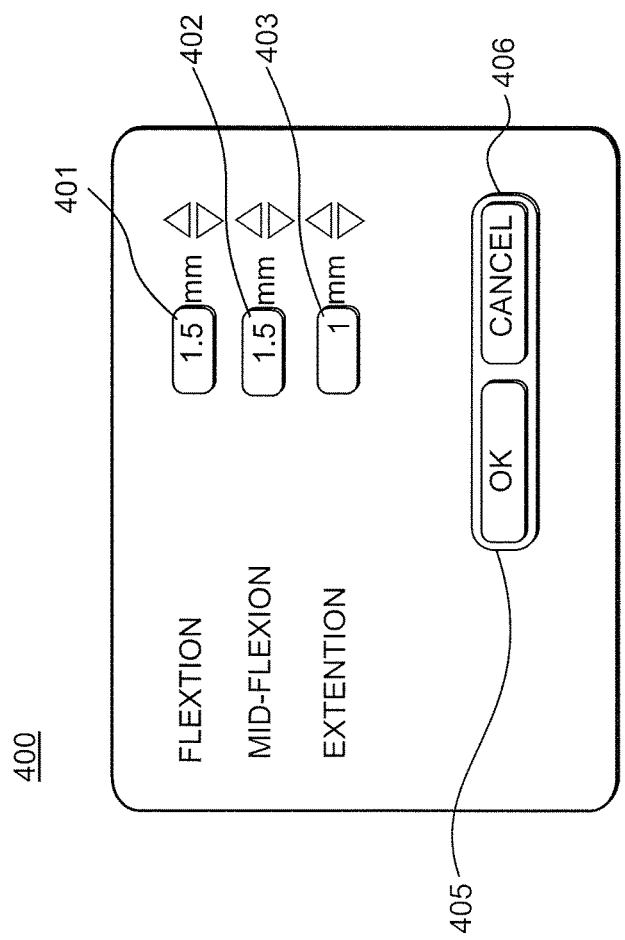
FIG. 4 illustrates an exemplary user interface, consistent with disclosed embodiments.

As discussed above, computer system 200 may also be configured to receive desired looseness values from a user, e.g., a surgeon. FIG. 4 discloses an exemplary user interface 400 that may be displayed on display 206A, for example, to allow the surgeon to enter the desired looseness values. User interface 400 includes three desired looseness value input fields 401, 402, and 403 that allow the surgeon to define desired looseness values at near −90° flexion, mid-flexion, and near −0° flexion, respectively. For example, the surgeon may enter numerical values into input fields 401, 402, and 403, and/or may choose the values using the arrows to the right of each respective input.

As shown in FIG. 4, the looseness values may be entered by the user as desired separation distances between femoral prosthetic component 110 and tibial prosthetic component 120 at different flexion values. For example, in user interface 400, the user has selected a 1.5 mm desired separation distance at 90° flexion, a 1.5 mm desired separation distance at mid-flexion (e.g., near −45° flexion), and a 1 mm desired separation distance at full extension (e.g., near −0° flexion).

Three inputs are shown in FIG. 4. However, in certain embodiments, computer system 200 may generate a user interface with an input field for each flexion position in which a computer system 200 recorded relative position data of femur 102 and tibia 101 (or tibial prosthetic component 120). For example, if a surgeon recorded relative positions between femur 102 and tibia 101 (or tibial prosthetic component 120) at four different flexion positions, as shown in FIG. 3, the surgeon may be able to enter four desired looseness values, each one corresponding to one of the flexion positions. In another embodiment, the surgeon may be limited to three values. In this embodiment, if the surgeon records relative positions at more than three flexion positions, all but three sets of relative position data may be discarded. For example, computer system 200 may maintain the sets of relative position data at the three flexion positions closest to 0°, 45°, and 90° flexion, respectively, and may discard the other sets of data. Alternatively, relative position data from one or more positions in the mid-flexion range, e.g., positions 322 and 323, may be averaged, interpolated, or otherwise combined to form a single relative position value close to a mid-flexion point, e.g., at near −45° flexion.

User interface 400 may also include "OK" button 405 and "Cancel" button 406. When the surgeon is satisfied with the looseness values, the surgeon may select "OK" button 405. Otherwise the surgeon may select "Cancel" button 406. Selecting "OK" button 405 may send the desired looseness values to computer system 200, enabling computer system 200 to determine a proposed orientation for a prosthetic component based on the desired looseness values entered by the user and the relative position data between femur 102 and tibia 101 (or tibial prosthetic component 120) recorded by system 200.

Figure 5:
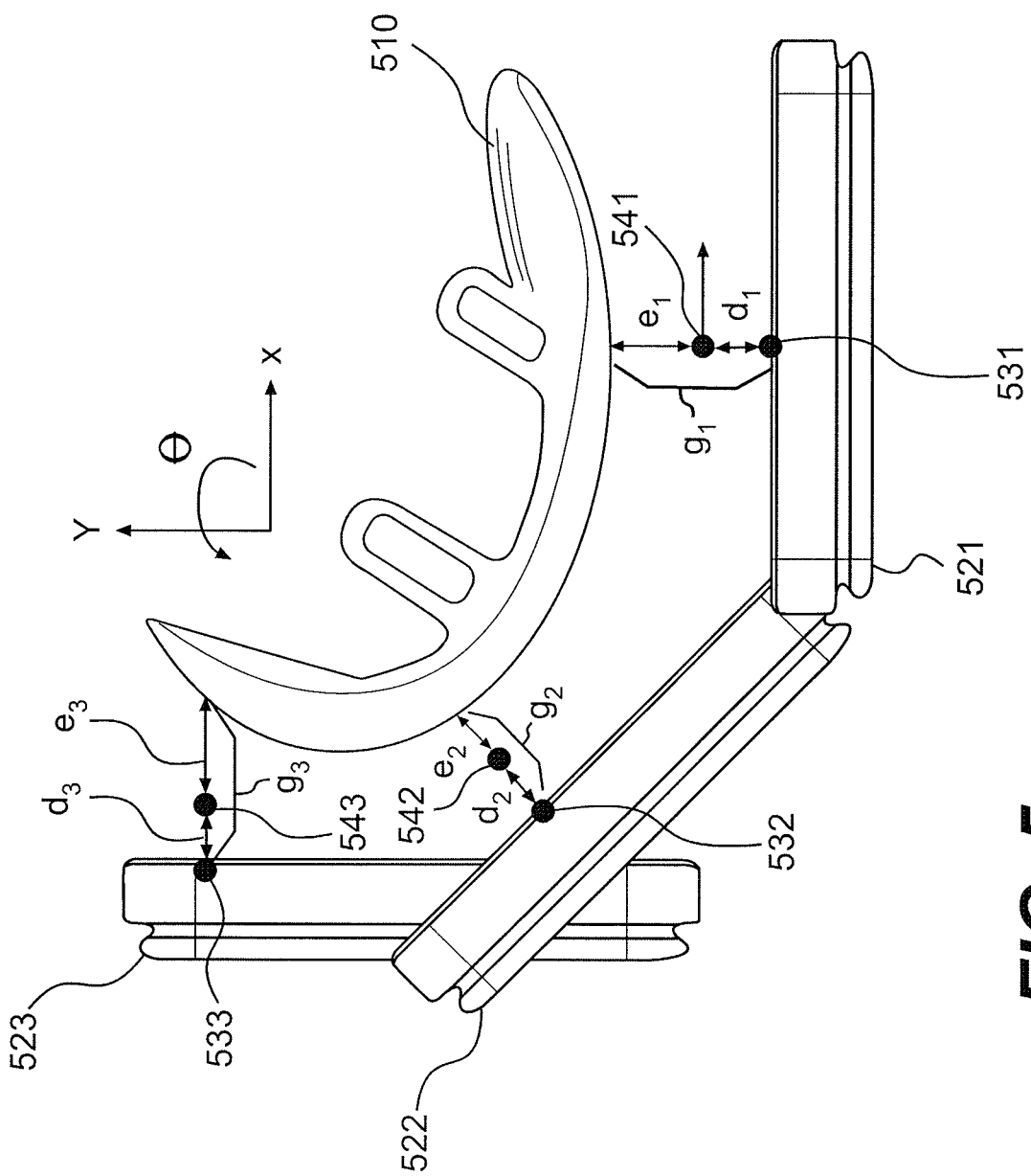
FIG. 5 is a pictorial illustration representing the relative positioning of a three-dimensional femoral prosthetic component model and a three-dimensional tibial prosthetic component model at multiple different flexion positions, consistent with certain disclosed embodiments.

FIG. 5 is a pictorial illustration representing the relative positioning of a three-dimensional femoral prosthetic component model 510 and a three-dimensional tibial prosthetic component model 520 at multiple different flexion positions 521-523, consistent with certain disclosed embodiments. Femoral prosthetic component model 510 may be a three-dimensional model for femoral prosthetic component 110, and tibial prosthetic component model 520 may be a three-dimensional model for tibial prosthetic component 120, for example. FIG. 5 illustrates how computer system 200 incorporates the three-dimensional models stored, e.g., in database 205, recorded relative position data between femur 102 and tibia 101, and the desired looseness values to determine one or more orientation parameter values of a prosthetic component.

Computer system 200 may determine the location of tibial prosthetic component model 520 at near −0° flexion position 521 based on the relative position data recorded at near −0° flexion, discussed above with regard to FIG. 3. Likewise, computer system 200 may determine the locations of tibial prosthetic component model 520 at near −45° flexion position 522 and near-90° flexion position 523 based on the relative position data recorded at near −45° flexion and near −90° flexion, respectively.

As discussed above with regard to FIG. 3, computer system 200 may record the relative position data before or after resection and installation of tibial prosthetic component 520. If computer system 200 records the relative position data after resection and installation, then the recorded position points 531-533 for each position 521-523 may correspond to the recorded relative position data that was recorded along tibial prosthetic component 520 discussed above with regard to FIG. 3. On the other hand, if computer system 200 records the relative position data before resection and installation, then computer system 200 may calculate the recorded position points 531-533 for each flexion position 521-523 based on the recorded relative position data recorded along tibia 101 in FIG. 3, an installation plan for tibial prosthetic component 120 (e.g., planned resection depth, etc.), and a known size (e.g., thickness) and shape of tibial prosthetic component 120.

Recorded position points 531-533 may be determined, e.g., based on the three-dimensional models of tibial prosthetic component 120 and/or tibia 101. For example, points 531-533 may correspond to anatomical landmarks of tibia 101 that may be stored in database 205, as discussed above. Similarly, points 531-533 may correspond to points on tibial prosthetic component 120 or tibia 101 that are located closest to femur 102. In still other embodiments, points 531-533 may be determined based on the geometry of tibial prosthetic component 120, e.g., they may be determined to be located at the centroid of tibial component 120, or at some other position with respect to tibial component 120.

Computer system 200 may also determine target value points 541-543 for each flexion position 521-523 by adding the desired looseness value for each flexion position 521-523 to the recorded position points 531-533 of each flexion position 521-523. For example, a surgeon may have entered a looseness value of $d_1$ for near −0° flexion, as discussed above with regard to FIG. 4. Thus, computer system 200 may generate a target value point 541 for near −0° flexion position 521 that is a distance $d_1$ from the recorded position point 531 in a direction substantially perpendicular to the surface of tibial prosthetic component model 520 at near −0° flexion position 521. Likewise, if the surgeon enters desired looseness values of $d_2$ and $d_3$ for 45° flexion and 90° flexion, respectively, then computer system 200 may similarly generate a target value point 542 $d_2$ mm from the recorded position point 532 for near −45° flexion position 522 in a direction substantially perpendicular to the surface of tibial prosthetic component model 520 at near −45° flexion position 522, and a target value point 543 $d_3$ mm from the recorded position point 533 for near −90° flexion position 523 in a direction substantially perpendicular to the surface of tibial prosthetic component model 520 at near −90° flexion position 523.

Target value points 541-543 generated by computer system 200 may correspond to, e.g., a target location for a point on the surface of femoral prosthetic component model 510. Thus, computer system 200 may implement one or more algorithms to change the orientation of femoral prosthetic component model 510 in one or more directions and about one or more axes in order to achieve a close fit between the surface of femoral prosthetic component model 510 and the target value points 541-543. For example, computer system 200 may implement one or more algorithms, examples of which are discussed below, to compare estimated separation distance values $g_1$, $g_2$, and/or $g_3$, which may be estimated by computer system 200, with their respective desired separation distance values $d_1$, $d_2$, and/or $d_3$, in order to minimize separation distance errors $e_1$, $e_2$, and/or $e_3$. Based on these algorithms, computer system 200 may determine a recommended position and orientation for femoral prosthetic component model 510 relative to a model of the femur, and hence, femoral prosthetic component 110 relative to the femur 102.

In another embodiment, an arbitrary number n of different flexion positions are collected. The estimated separation distance values $g_1$, $g_2$, ... $g_n$, are computed as the minimum distance between the surfaces of the three-dimensional femoral prosthetic component model 510 and the three-dimensional tibia prosthetic component model 520. The minimum separation distance is an estimate of the physical separation distance between the femoral and tibial prosthetic components. In this embodiment, n corresponding distance values $d_1$, $d_2$, ... $d_n$ may also be entered and/or otherwise collected, and n distance errors $e_1$, $e_2$, ... $e_n$ may be calculated as discussed above.

In certain embodiments, computer system 200 may control one or more orientation parameters to change the orientation of femoral prosthetic component model 510 within the sagittal plane. For example, the position of femoral prosthetic component model 510 in FIG. 5 may correspond to the preliminary orientation determined by computer system 200 based on, e.g., the edge points and lowpoints of femoral prosthetic component model 510. Computer system 200 may then move femoral prosthetic component model 510 in two translational directions substantially within the sagittal plane (shown in FIG. 5 as the x-direction and the y-direction) by changing an orientation parameter value corresponding to each direction and may rotate femoral prosthetic component model 510 about an axis substantially orthogonal to the sagittal plane (shown in FIG. 5 as θ) by changing an orientation parameter value corresponding to the rotation about the axis.

In other embodiments, computer system 200 may change the orientation of femoral prosthetic component model 510 within one or more of the sagittal, coronal, and transverse planes. For example, in one embodiment, computer system 200 may move femoral prosthetic component model 510 in three substantially perpendicular directions (e.g., x-, y-, and z directions), by changing orientation parameter values for each direction, and rotate femoral prosthetic component model 510 about three substantially perpendicular axes (e.g., θ-, φ-, and ϕ-rotations), by changing orientation parameter values for rotation about each axis, so as to be able to orient femoral prosthetic component model 510 in any possible orientation.

An orientation parameter value may correspond to any type of information or value capable of determining a one or more aspects of a prosthetic component's position or orientation. For example, an orientation parameter value may include a point in a coordinate space, such as a two-dimensional or a three-dimensional space, or a translational value along an axis in the coordinate space. An orientation parameter value may also include a rotational value representing rotation about an axis. Moreover, orientation parameter values may include translational and/or rotational differences from a predetermined orientation. For example, an orientation parameter value may represent a difference between a preliminary orientation of a prosthetic component model and an estimated orientation of the prosthetic component in one or more directions or rotated about one or more axes. The above are merely examples, however, and those skilled in the art will appreciate that orientation parameter values may be represented in many other ways.

An exemplary algorithm for determining an orientation of femoral prosthetic component model 510 that may be employed by computer system 200 includes generating a cost function that includes one or more orientation parameter values as variable inputs and outputs a cost based on a difference between one or more estimated separation distances and one or more first desired separation distances, respectively.

In one embodiment, the cost function may be defined as:

$$C = \sum_{i=1}^{n} (w_i c_i) + c_x + c_y + c_\theta \quad (1)$$

where i represents a particular flexion position, n represents the total number of flexion positions that may be collected, $w_i$ is a weighting variable that may be applied for each flexion position, $c_i$ is a cost function for each flexion position, $c_x$ is a cost function for moving femoral prosthetic component model 510 in a first translational direction substantially parallel to the sagittal plane (e.g., the x-direction), $c_y$ is a cost function for moving prosthetic component 510 in a second translational direction substantially parallel to the sagittal plane (e.g., the y-direction), and $c_\theta$ is a cost function for rotating femoral prosthetic component model 510 about an axis substantially perpendicular to the sagittal plane (e.g., a θ-rotation). As discussed above, any number n of flexion positions may be collected. Weighting variables $w_i$ may allow a user or system controller to weight the relative importance of the separation distance at each flexion position. In certain embodiments weighting variables $w_i$ may be predetermined. In other embodiments, weighting variables $w_i$ may be configurable by a user, e.g., a surgeon.

The cost functions of equation (1), $c_i$, $c_x$, $c_y$, and $c_\theta$, may be defined as:

$c_i = e_i$, if $|e_i| \leq t_i$ $c_i = K(e_i - t_i) + t_i$, if $|e_i| > t_i$ \quad (2)

$c_x = 0$, if $|\Delta x| \leq t_x$ $c_x = K(|\Delta x| - t_x)$, if $|\Delta x| > t_x$ \quad (3)

$c_y = 0$, if $|\Delta y| \leq t_y$ $$c_y = K(|\Delta y| - t_y), \text{ if } |\Delta y| > t_y \quad (4)$$

$$c_\theta = 0, \text{ if } |\Delta \theta| \le t_\theta$$

$$c_\theta = K(|\Delta \theta| - t_\theta), \text{ if } |\Delta \theta| > t_\theta \quad (5)$$

where $|e_i|$ represents the absolute value of the difference between the estimated separation distance and the desired separation distance between tibial prosthetic component model 520 and femoral prosthetic component model 510 at a particular flexion position i (e.g., $|e_1|=|g_1-d_1|$ as shown in FIG. 5); K represents a constant value; $t_i$ represents a separation distance tolerance for a flexion position i, $\Delta x$, $\Delta y$, and $\Delta \theta$ represent orientation parameter values for the first translational direction substantially parallel to the sagittal plane, the second translational direction substantially parallel to the sagittal plane, and the rotational value about the axis substantially perpendicular to the sagittal plane; and $t_x$, $t_y$, and $t_\theta$ represent displacement tolerances in each respective direction.

Constant value K may be a large number, e.g., 1,000,000, so as to cause a steep cost increase in the cost functions when a separation distance or a displacement amount exceeds a corresponding threshold value. Tolerance values $t_x$, $t_y$, and $t_\theta$ may be determined by a user or may be predetermined. In one embodiment, $t_x$, $t_y$, and $t_\theta$ may be set to 10 mm, 10 mm, and 5°, respectively. Likewise, tolerance values $t_i$ for each flexion position i may be determined by a user or may be predetermined. In one embodiment, tolerance values $t_i$ corresponding to the near-0° and near −90° flexion positions may be set to ±0.25 mm and tolerance values $t_i$ corresponding to all other flexion positions may be set to ±1.00 mm.

While the cost function shown above in equation (1) outputs a cost based on three potential inputs, namely two translational orientation parameter values and one rotational orientation parameter value, those skilled in the art will appreciate that equation (1) can be modified to include additional orientation parameter values. For example, equation (1) may be modified to include an additional translational orientation parameter value and two additional rotational orientation parameter values by adding cost functions $c_z$, $c_\varphi$, and $c_\theta$ similar to the cost functions of equations (3)-(5).

Likewise, equation (1) may be modified to include fewer orientation parameter values by removing the respective cost function corresponding to the orientation parameter value(s) to be removed. For example, computer system 200 may modify equation (1) to include only the cost functions for the x and y translational orientation parameters. In this embodiment, computer 200 may optimize the x and y translational orientation parameter values for a given rotational orientation parameter.

As discussed above, the cost function $c_i$ for each flexion position described in equation (2) may include a piecewise equation with two piecewise portions. In certain embodiments, the cost function $c_i$ for each flexion position may be modified to include a piecewise equation with more than two piecewise portions. Moreover, the cost function $c_i$ may be modified such that the piecewise portions are determined based on the value of $e_i$ rather than the absolute value of $e_i$ (e.g., $e_1 = g_1 - d_1$ as shown in FIG. 5). For example, the cost function $c_i$ may be represented as shown in equation (6):

$$c_i = K_1(t_{1,i} - e_i) + K_2 t_{1,i}, \text{ if } e_i \le t_{1,i}$$

$$c_i = K_2(-e_i), \text{ if } t_{1,i} < e_i \le 0$$

$$c_i = K_3 e_i, \text{ if } 0 < e_i \le t_{2,i}$$

$$c_i = K_4(e_i - t_{2,i}) + K_3 t_{2,i}, \text{ if } t_{2,i} < e_i \quad (6)$$

Constant values $K_1$ ... $K_4$ may be large numbers, e.g., 1,000,000, so as to cause a steep cost increase in the cost functions when a separation distance or a displacement amount exceeds a corresponding threshold value. In one embodiment, $K_1$, $K_2$, $K_3$, and $K_4$ may be set to 1,000,000, 5,000, 0, and 1,000,000, respectively. Tolerance values $t_{1,i}$, and $t_{2,i}$, may be determined by a user or may be predetermined. In one embodiment, $t_{1,i}$, and $t_{2,i}$, may be set to −5 mm and 2 mm, respectively.

Equation (6) may be used to determine a cost $c_i$ for points at each flexion position collected. For example, equation (6) may be used to determine a cost $c_i$ for each of points 531-533 shown in FIG. 5, and for any other points or number of points. For example, in certain embodiments, equation (6) may be used to determine a cost $c_i$ at a point on the anterior tip area of femoral prosthetic component model 510. Computer system 200 may use equation (6) to calculate the cost $c_i$ for each flexion position to be used in conjunction with equation (1), discussed above.

Computer system 200 may implement one or more optimization algorithms to determine orientation parameter values that minimize the cost function of equation (1). For example, computer system 200 may apply one or more nonlinear optimization techniques such as the Nelder-Mead simplex search to determine sets of orientation parameter values that produce one or more local minima for the cost function of equation (1). Computer system 200 may output the sets of orientation parameter values as potential orientations for femoral prosthetic component model 510.

In certain embodiments, computer system 200 may implement an optimization algorithm that determines translational parameter values that minimize the cost function of equation (1) for a particular rotational angle $\theta_i$. Computer system 200 may then rotate femoral prosthetic component model 510 about an axis perpendicular to the sagittal plane by a predetermined increment, and then repeat the process of minimizing the cost function of equation (1) for the new rotational angle $\theta_{i+1}$. Computer system 200 may repeat this process for multiple different angles, and may choose the rotational angle $\theta$ and corresponding x and y translational orientation parameter values that result in the minimum cost function value as the orientation for femoral prosthetic component model 510, and hence, femoral prosthetic component 110.

Another exemplary algorithm for determining an orientation of femoral prosthetic component model 510 (and, hence, femoral prosthetic component 110) that may be employed by computer system 200 includes minimizing a difference between one or more desired separation distances and estimated separation distances at one or more flexion positions, respectively. For example, in an embodiment where the relative positions of femur 102 and tibia 101 are recorded for three different flexion positions, the exemplary algorithm may move femoral prosthetic component model 510 in the x- and y-directions as shown in FIG. 5, to determine translational orientation parameter values in the x- and y-directions that minimize values $e_1$ and $e_3$, for a particular rotational angle, $\theta_i$. Computer system 200 may calculate the value of $e_2$ at the translational orientation parameter values in the x- and y-direction for the particular rotational angle $\theta_i$. Computer system 200 may then rotate femoral prosthetic component model 510 by a predetermined increment, and then repeat the process of minimizing $e_1$ and $e_3$ and measuring $e_2$ for the new rotational angle $\theta_{i+1}$. Computer system 200 may repeat this process for multiple different angles, and may choose the rotational angle θ and corresponding x and y translational orientation parameter values that have the minimum displacement $e_2$ as the orientation for femoral prosthetic component model 510, and hence, femoral prosthetic component 110. This algorithm is described in greater detail below with respect to FIG. 7.

After computer system 200 has determined the orientation for femoral prosthetic component model 510, and hence, femoral prosthetic component 110, it may output the orientation via display device 206A or other I/O device 206. For example, computer system 200 may be configured to display an image of a femoral prosthetic component model 510 overlaying three-dimensional model of the patient's femur, and may orient the femoral prosthetic component model 510 over the patient's femur model according to the orientation information. Moreover, computer system 200 may also display information informing the user, e.g., a surgeon, where to implant the prosthetic component relative to one or more predetermined markers on the femur. Such information may also include an indication of how much bone to resect to properly orient the femoral prosthetic component, a number, location, and size of holes to form in the femur in order to secure the femoral prosthetic component, etc.

Figure 6:
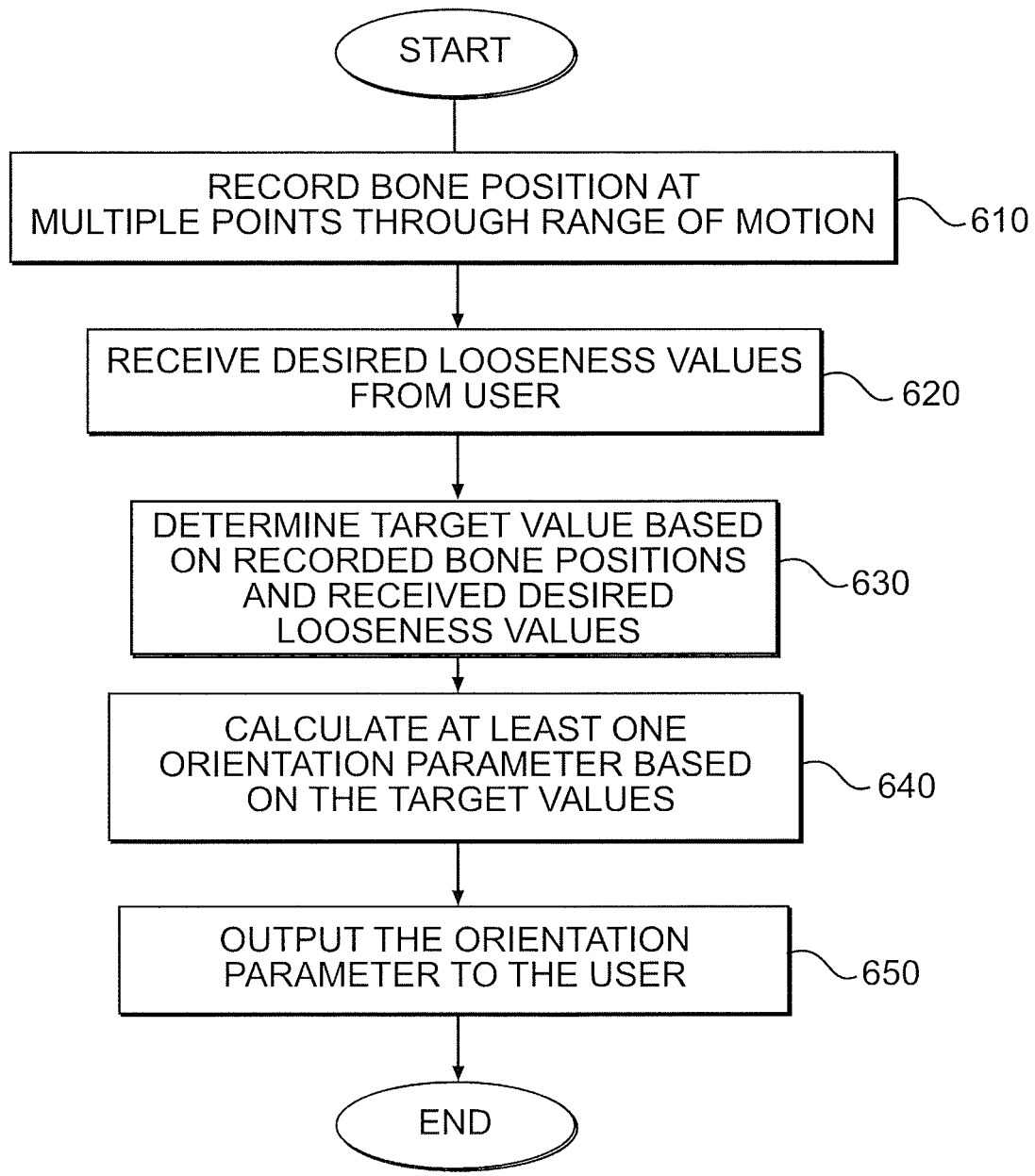
FIG. 6 is a flowchart illustrating an exemplary process for determining prosthetic component orientation, consistent with disclosed embodiments.

FIG. 6 is a flowchart illustrating an exemplary process for determining prosthetic component orientation, consistent with disclosed embodiments. The process may be performed, e.g., by computer system 200. As shown in FIG. 6, computer system 200 may record relative bone positions in the knee joint through a range of motion (step 610). For example, as discussed above, a surgeon may apply a valgus/varus moment to the knee joint 100 and computer system 200 may record the relative positions between the femur 102 and the tibia 101 (or tibial prosthetic component 120) at one or more flexion positions through the patient's range of motion.

Computer system 200 may also receive desired looseness values from the user, e.g., the surgeon (step 620). In some embodiments, the looseness values may be expressed as a desired separation distance between a femoral prosthetic component 110 and a tibial prosthetic component 120 at one or more flexion positions of the knee joint 100.

Computer system 200 may then determine target values based on the recorded bone positions and the received desired looseness values (step 630). For example, computer system 200 may modify the recorded bone positions based on the received desired looseness values to determine the target values. The target values may correspond to, e.g., a target location for a point on the surface of a prosthetic component.

Computer system 200 may also calculate at least one orientation parameter value based on the target values (step 640). For example, as discussed above, computer system 200 may implement one or more algorithms to calculate at least one orientation parameter value for the prosthetic component. In some embodiments, computer system 200 may calculate three or more orientation parameter values. If computer system 200 calculates three orientation parameter values, those parameter values may include two translational orientation parameter values and one rotational orientation parameter value that specify an orientation of the prosthetic component in the sagittal plane. In certain embodiments, computer system 200 may implement one or more algorithms to calculate orientation parameter values such that a cost function, e.g., as shown in equation (1) is minimized.

Computer system 200 may output the at least one orientation parameter value to the user (step 650). For example, computer system 200 may output the orientation parameter value to the user as a numerical value, e.g., a translational distance by which to move the prosthetic component. In other embodiments, computer system 200 may output one or more orientation parameter values as an image of the three-dimensional model for the femoral prosthetic component 110 overlaying the three-dimensional model of the patient's femur, and may orient the femoral prosthetic component model 510 over the patient's femur model according to the orientation information.

Figure 7:
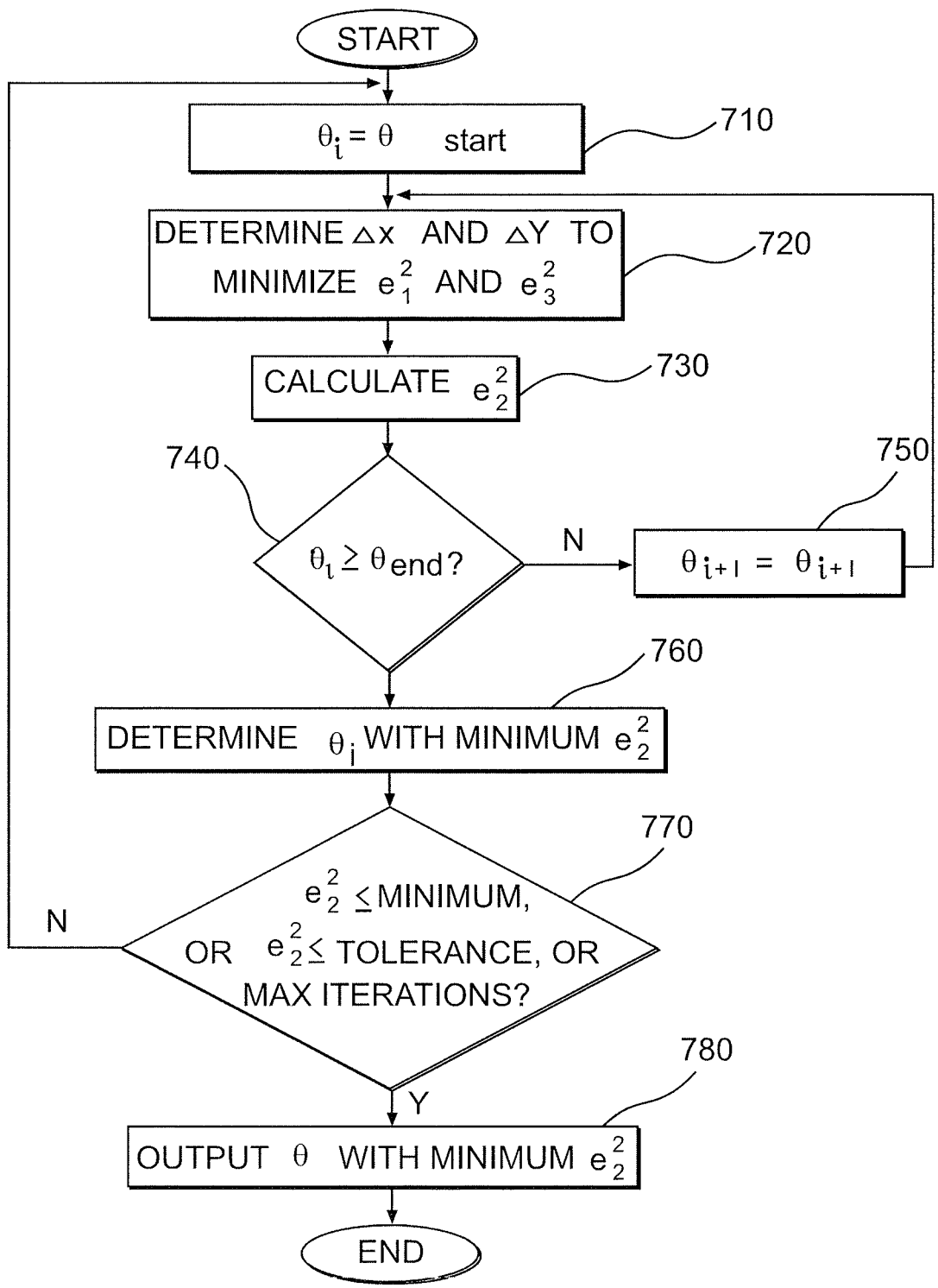
FIG. 7 is a flowchart illustrating another exemplary process for determining prosthetic component orientation, consistent with disclosed embodiments.

FIG. 7 is a flowchart illustrating an exemplary process for determining prosthetic component orientation, consistent with disclosed embodiments. The process may be performed by computer system 200, e.g., as a part of step 640 in FIG. 6. For example, FIG. 7 illustrates a process for determining prosthetic component orientation by minimizing differences between desired separation distances and estimated separation distances between a femoral prosthetic component 110 and a tibial prosthetic component 120 at two different flexion positions. As discussed above, computer system 200 may perform such calculations using, e.g., one or more three-dimensional models, such as three-dimensional models 510 and 520 of FIG. 5. In one embodiment, the two different flexion positions may be a near −0° flexion position and a near −90° flexion position, although other flexion positions may be used.

Computer system 200 may initialize a rotational orientation parameter value $θ_i$ to a predetermined value, $θ_{start}$ (step 710). In one embodiment, $θ_{start}$ may be set to −5°, although any value may be used.

Computer system 200 then determines the x and y translational orientation parameter values that minimize the squares of a difference, $e_1$, between a desired separation distance $d_1$ and an estimated separation distance $g_1$ for a first flexion position, and a difference, $e_3$, between a desired separation distance $d_3$ and an estimated separation distance $g_3$ for a third flexion position (step 720). For example, computer system 200 may use any type of optimization technique, such as any combination of linear or non-linear optimization, curve fitting analysis, regression analysis, etc., to minimize $e_1$ and $e_3$.

Computer system 200 may then calculate the square of the difference, $e_2$, between a desired separation distance and an estimated separation distance for a second flexion position at the x and y translational orientation parameter values determined in step 720 (step 730). In one embodiment, $e_1$ may be determined at a near −0° flexion position, $e_3$ may be determined at a near-90° flexion position, and $e_2$ may be determined at some flexion position in between 0° and 90°.

Computer system 200 may then determine if the current rotational orientation parameter value $θ_i$ is greater than or equal to a predetermined value $θ_{end}$ (step 740). In one embodiment, $θ_{end}$ may be set to 5°, although any value may be used. If computer system 200 determines that $θ_i$ is not greater than or equal to a predetermined value $θ_{end}$ (step 740, N), computer system 200 may increment $θ_i$ by 1°, e.g. may rotate femoral prosthetic component model 510 by 1° (step 750) and return to step 720, wherein steps 720-750 repeat until $θ_i$ is greater than or equal to a predetermined value $θ_{end}$. Of course, $θ_i$ can be incremented by any other value, such as 0.25°, 0.5°, 2°, etc.

If, on the other hand, computer system 200 determines that $θ_i$ is greater than or equal to a predetermined value $θ_{end}$ (step 740, Y), computer system 200 may determine which one of the $θ_i$ values has the minimum corresponding $(e_2)^2$ value (step 760).

Computer system 200 may then determine whether the minimum corresponding $(e_2)^2$ value from step 760 satisfies one or more requirements, such as being equal to a predetermined minimum or tolerance value, or whether a maximum number of iterations have been reached (step 770). If the minimum corresponding $(e_2)^2$ value is not equal to or less than a predetermined minimum or tolerance value and if the maximum number of iterations have not been reached (step 770, N), then the process returns to step 710 where another iteration is performed. If another iteration is performed, computer system 200 may use one or more learning or genetic algorithms to choose different values for the x and y translational orientation parameter values for each $\theta_i$ in a subsequent iteration, so as to converge on x and y translational orientation parameter values that result in an $(e_2)^2$ value less than a threshold or minimum value. The predetermined minimum or tolerance value in step 770 may or may not be customizable by a user. In one embodiment the predetermined minimum or tolerance value may be set to 0.5 mm. Likewise the maximum iterations value may or may not be customizable by a user. In one embodiment the maximum iterations value may be set to 50 iterations.

If, on the other hand, computer system 200 determines that the corresponding $(e_2)^2$ value is equal to or less than a predetermined minimum or tolerance value, or a maximum number of iterations have been reached (step 770, Y), then computer system 200 may output the $\theta_i$ rotational orientation parameter value and the x and y translational orientation parameter values that correspond to the $(e_2)^2$ value (step 780).

Systems and methods described herein provide a solution for determining an orientation for one or more prosthetic components to be used in a surgery such as an unicompartmental arthroplasty. Presently disclosed methods and systems may have several advantages. For example, systems and methods may allow a user, such as a surgeon, to enter desired looseness values for a knee joint and receive suggestions for orientations of one or more prosthetic components based on the desired looseness values. Thus, the methods and systems may save the surgeon time and effort, resulting in shorter surgery times and less pre-operative planning time on the surgeon's part. Moreover, the methods and systems may facilitate proper orientation of one or more prosthetic components, resulting in proper knee joint articulation, which may in turn increase the life expectancy of the prosthetic components.

The foregoing descriptions have been presented for purposes of illustration and description. They are not exhaustive and do not limit the disclosed embodiments to the precise form disclosed. Modifications and variations are possible in light of the above teachings or may be acquired from practicing the disclosed embodiments. For example, the described implementation includes software, but the disclosed embodiments may be implemented as a combination of hardware and software or in firmware. Examples of hardware include computing or processing systems, including personal computers, servers, laptops, mainframes, microprocessors, and the like. Additionally, although disclosed aspects are described as being stored in a memory, one skilled in the art will appreciate that these aspects can also be stored on other types of computer-readable storage devices, such as secondary storage devices, like hard disks, floppy disks, a CD-ROM, USB media, DVD, or other forms of RAM or ROM.

Other embodiments will be apparent to those skilled in the art from consideration of the specification and practice of the embodiments disclosed herein. The recitations in the claims are to be interpreted broadly based on the language employed in the claims and not limited to examples described in the present specification or during the prosecution of the application, which examples are to be construed non-exclusively. Further, the steps of the disclosed methods may be modified in any manner, including by reordering, combining, separating, inserting, and/or deleting steps. It is intended, therefore, that the specification and examples be considered as exemplary only, with a true scope and spirit being indicated by the following claims and their full scope equivalents.

What is claimed is:

1. A computer-implemented method for determining an orientation parameter value of a prosthetic component, the method comprising:

using a virtual model of a flexing joint comprising a first bone and a second bone and a virtual model of a first prosthetic component to determine a planned preliminary orientation of the first prosthetic component in the joint;

receiving, at an input device coupled to a processor, an input from a user descriptive of a first desired separation distance between the first prosthetic component and a second prosthetic component at a first flexion position of the joint;

determining, using a tracking or imaging system, relative positions of the first bone and the second bone at a plurality of flexion positions of the joint;

recording, by the processor, positional data of the first bone and the second bone determined using the tracking or imaging system when the joint is in the first flexion position;

estimating, based on the positional data, a first estimated separation distance between the first prosthetic component and the second prosthetic component at the first flexion position of the joint for at least one potential orientation of the first prosthetic component;

determining a first error value as the different between the first desired separation distance and the first estimated separation distance;

determining a first orientation parameter value of the first prosthetic component that minimizes the first error value;

displaying, on a display, the first orientation parameter value;

moving the virtual model of the first prosthetic component in the model of the joint according to the first orientation parameter value to update the planned preliminary orientation of the first prosthetic component; and providing to the user a location for implanting the first prosthetic component on the associated first bone or second bone according to the first orientation parameter value.

2. The computer-implemented method of claim 1, further comprising:

receiving a second desired separation distance between the first prosthetic component and the second prosthetic component at a second flexion position of the joint;

receiving a third desired separation distance between the first prosthetic component and the second prosthetic component at a third flexion position of the joint;

estimating a second estimated separation distance between the first prosthetic component and the second prosthetic component at the second flexion position of the joint for the at least one potential orientation of the first prosthetic component;

estimating a third estimated separation distance between the first prosthetic component and the second prosthetic component at the third flexion position of the joint for the at least one potential orientation of the first prosthetic component determining a second and a third error value as the difference between the second and third estimated separation distances to the second and third desired separation distances, respectively; and determining the first orientation parameter value that minimizes at least one of the first, second, or third error values.

3. The computer-implemented method of claim 2, further comprising:

determining a second orientation parameter value and a third orientation parameter value of the first prosthetic component that minimizes the second error value and the third error value, respectively.

4. The computer-implement method of claim 2, wherein determining the first orientation parameter value comprises:

selecting a preferred error value to minimize out of the first, second, and third error value; and determining the first orientation parameter that minimizes the preferred error value.

5. The computer-implemented method of claim 3, wherein the first orientation parameter value and the second orientation parameter value each represents a translation along an axis in a sagittal plane, and the third orientation parameter value represents a rotation about an axis substantially perpendicular to the sagittal plane.

6. The computer-implemented method of claim 5, further including:

determining fourth, fifth, and sixth orientation parameter values that minimizes the first, second, and third error values, respectively, wherein the fourth orientation parameter value represents a translation along an axis substantially perpendicular to the sagittal plane, the fifth orientation parameter value represents a rotation about an axis substantially perpendicular to a coronal plane, and the sixth orientation parameter value represents a rotation about an axis substantially perpendicular to a transverse plane.

7. The computer-implemented method of claim 2, further comprising:

determining a second orientation parameter value, wherein determining the first orientation parameter value and the second orientation parameter value of the first prosthetic component further includes:

generating a cost function that includes, as first and second inputs, the first and second orientation parameter values, respectively, and that has a cost based on both a difference between the first estimated separation distance and the first desired separation distance and a difference between the second estimated separation distance and the second desired separation distance;

determining a local minimum for the cost function; and determining the first and second orientation parameter values to be the values of the first and second inputs at the local minimum of the cost function.

8. The computer-implemented method of claim 4, wherein determining the first, second, and third orientation parameter values of the first prosthetic component further include:

generating a cost function that includes, as first, second, and third inputs, the first, second, and third orientation parameter values, respectively, and that has a cost based on a difference between the first estimated separation distance and the first desired separation distance, a difference between the second estimated separation distance and the second desired separation distance, and a difference between the third estimated separation distance and the third desired separation distance;

determining a local minimum for the cost function; and determining the first, second, and third orientation parameter values to be the values of the first, second, and third inputs at the local minimum of the cost function.

9. The computer-implemented method of claim 5, wherein determining the first, second, and third orientation parameter values of the first prosthetic component further include:

for each of a plurality of potential third orientation parameter values:

determining a potential first orientation parameter value and a potential second orientation parameter value so as to minimize a difference between the first estimated separation distance and the first desired separation distance and so as to minimize a difference between the third estimated separation distance and the third desired separation distance; and calculating a difference between the estimated second separation distance and the desired second separation distance;

comparing the calculated difference between the estimated second separation distance and the desired second separation distance for each of the plurality of potential third orientation parameter values to determine the potential third orientation parameter value corresponding to the smallest calculated difference; and determining that the potential third orientation parameter value and its corresponding potential first and second orientation parameter values that correspond to the smallest calculated difference are the first, second, and third orientation parameter values, if the smallest calculated difference is less than a threshold difference.

10. The computer-implemented method of claim 1, wherein the first prosthetic component is one of a medial or lateral unicompartmental implant.

11. A system for determining an orientation parameter value of a prosthetic component, the system comprising:

an input device configured to receive a first desired separation distance between a first prosthetic component and a second prosthetic component at a first flexion position of a flexion joint comprising a first bone and a second bone;

a tracking or imaging system configured to determine relative positions of the first bone and the second bone at a plurality of flexion positions of the joint;

a processor, operatively coupled to the input device and configured to:

determine a planned preliminary orientation of a first prosthetic component in the joint using a virtual model of the joint and a virtual model of the first prosthetic component;

record positional data of the first bone and the second bone determined using the tracking or imaging system when the joint is in the first flexion position;

estimate, based on the positional data, a first estimated separation distance between the first prosthetic component and a second prosthetic component at the first flexion position of the joint for at least one potential orientation of the first prosthetic component; and determine a first error value as the difference between the first desired separation distance and the first estimated separation distance;

determine a first orientation parameter value of the first prosthetic component that minimizes the first error value; and a display operatively coupled to the processor and configured to output the first orientation parameter value; and wherein the processor is further configured to move the virtual model of the first prosthetic component in the virtual model of the joint according to the first orientation parameter value to update the planned preliminary orientation of the first prosthetic component; and wherein the processor is further configured to provide to a user a location for implanting the first prosthetic component on the associated first bone or second bone according to the first orientation parameter value.

12. The system of claim 11, wherein the input device is further configured to:

receive a second desired separation distance between the first prosthetic component and the second prosthetic component at a second flexion position of the joint; and receive a third desired separation distance between the first prosthetic component and the second prosthetic component at a third flexion position of the joint; and the processor is further configured to:

estimate a second estimated separation distance between the first prosthetic component and the second prosthetic component at the second flexion position of the joint for the at least one potential orientation of the first prosthetic component; and estimate a third estimated separation distance between the first prosthetic component and the second prosthetic component at the third flexion position of the joint for the at least one potential orientation of the first prosthetic component determine a second and a third error value as the difference between the second and third estimated separation distances to the second and third desired separation distances, respectively; and determine the first orientation parameter value that minimizes at least one of the first, second, or third error values.

13. The system of claim 12, wherein the processor is further configured to:

determine a second orientation parameter value and a third orientation parameter value of the first prosthetic component that minimizes the second error value and the third error value, respectively.

14. The system of claim 13, wherein the first orientation parameter value and the second orientation parameter value each represents a translation along an axis substantially in a sagittal plane, and the third orientation parameter value represents a rotation about an axis substantially perpendicular to the sagittal plane.

15. The system of claim 13, wherein the processor is further configured to:

generate a cost function that includes, as first, second, and third inputs, the first, second, and third orientation parameter values, respectively, and that has a cost based on a difference between the first estimated separation distance and the first desired separation distance, a difference between the second estimated separation distance and the second desired separation distance, and a difference between the third estimated separation distance and the third desired separation distance;

determine a local minimum for the cost function; and determine the first, second, and third orientation parameter values to be the values of the first, second, and third inputs at the local minimum of the cost function.

16. The system of claim 14, wherein the processor is further configured to, for each of a plurality of potential third orientation parameter values:

determine a potential first orientation parameter value and a potential second orientation parameter value so as to minimize a difference between the first estimated separation distance and the first desired separation distance and so as to minimize a difference between the third estimated separation distance and the third desired separation distance;

calculate a difference between the estimated second separation distance and the desired second separation distance;

compare the calculated difference between the estimated second separation distance and the desired second separation distance for each of the plurality of potential third orientation parameter values to determine the potential third orientation parameter value corresponding to the smallest calculated difference; and determine that the potential third orientation parameter value and its corresponding potential first and second orientation parameter values that correspond to the smallest calculated difference are the first, second, and third orientation parameter values, if the smallest calculated difference is less than a threshold difference.

17. The system of claim 12, wherein the processor is further configured to:

select a preferred error value to minimize out of the first, second, and third error value; and determine the first orientation parameter that minimizes the preferred error value.

18. A computer-implemented method for determining an orientation of a prosthetic component, the method comprising:

determining, by a processor associated with a computer, a planned preliminary orientation of a first prosthetic component in a flexion joint using a virtual model of the joint comprising a first bone and a second bone, and a virtual model of the first prosthetic component;

determining, using a tracking or imaging system, relative positions of the first bone and the second bone at a plurality of flexion positions of the joint;

recording, by a processor associated with a computer, relative positions of the first bone and the second bone at the plurality of flexion positions determined using the tracking or imaging system;

receiving, from a user via a user interface, a plurality of looseness values, each of the plurality of looseness values corresponding to a looseness preference between the first prosthetic component and a second prosthetic component for one of the plurality of flexion positions of the joint;

determining a first error value based on the recorded relative positions of the first bone and the second bone, and the received looseness values;

determine an orientation of the first prosthetic component that minimizes the first error value;

displaying, on a display, the orientation of the first prosthetic component;

moving the virtual model of the first prosthetic component in the model of the joint according to the determined orientation to update the planned preliminary orientation of the first prosthetic component; and providing to the user a location for implanting the first prosthetic component on the associated first bone or second bone according to the determined orientation.

19. The computer-implemented method of claim 18, wherein determining the orientation of the prosthetic component includes:
   determining target value points based on the recorded relative positions of the first bone and the second bone and the received looseness values; and
   modifying an orientation of the model of the first prosthetic component to minimize a distance between the target points and a surface of the model of the first prosthetic component.

20. The computer-implemented method of claim 18, wherein the orientation of the first component includes two translational values each along an axis substantially in the sagittal plane, and a rotational value about an axis substantially perpendicular to the sagittal plane.

* * * * *